United States Patent [19]

Ecke, Jr.

[11] Plant 4,860

[45] Jun. 22, 1982

[54] VARIEGATED POINSETTIA NAMED V-14 JB

[75] Inventor: Paul Ecke, Jr., Encinitas, Calif.

[73] Assignee: Paul Ecke Ranch, Encinitas, Calif.

[21] Appl. No.: 194,756

[22] Filed: Oct. 7, 1980

[51] Int. Cl.[3] ..... A01H 5/00
[52] U.S. Cl. ..... Plt./86
[58] Field of Search ..... Plt./86

[56] References Cited

U.S. PATENT DOCUMENTS

P.P. 3,889 5/1976 Fantom ..... Plt./86

*Primary Examiner*—James R. Feyrer
*Attorney, Agent, or Firm*—Charles W. Rummler

[57] ABSTRACT

A new poinsettia cultivar having the unique physical and growth characteristics of the variety named Poinsettia V-14 (U.S. Plant Pat. No. 4,384), now named Glory, except that this new plant has its red bracts flecked and streaked with pink.

1 Drawing Figure

BACKGROUND OF THE NEW PLANT

This new poinsettia plant originated as a mutation of its parent, Poinsettia V-14, U.S. Plant Pat. No. 4,384, and was discovered by me in 1979 in my greenhouse at Encinitas, Calif., during the course of many trials and attempts to obtain new varieties having commercial merit and also retaining the advantageous characteristics of the parent variety. Upon my selection of this new plant, I reproduced it by means of cuttings for test purposes at Encinitas, Calif., and clones of this plant were subjected to successive generations of propagation which demonstrated that its distinctive characteristics hold true from generation to generation and appear to be firmly fixed.

DESCRIPTION OF THE DRAWING

My new poinsettia plant is illustrated by the accompanying full color photographic drawing, which shows flowers and bracts of the new plant in full bloom, the colors shown being as nearly true as it is reasonably possible to achieve by conventional professional photographic procedures.

DESCRIPTION OF THE NEW PLANT

The following is a detailed description of my new poinsettia variety based upon observations made in greenhouse at Encinitas, Calif., during the early months of 1980, the color designations being as close as possible to the colors of the R.H.S. Colour Chart published by The Royal Horticultural Society of London, England.

THE PLANT

Origin: Mutation.
Parentage: Poinsettia V-14 (U.S. Plant Pat. No. 4,384).
Classification:
*Botanic.—Euphorbia pulcherrima.*
Form: Shrub.
Height: Medium.
Growth habit:
*As a single stem.*—Upright and vigorous with self-branching side shoots; may require a growth regulator.
*As a branched plant.*—Upright with very many stems producing a bushy, full appearance.
Growth rate: Very fast. Under automatic mist, rooting occurs in 10 to 15 days. The plant will bloom in about 9 to 10 weeks at a night temperature of 17° to 19° C. during October and November. A somewhat higher temperature may be necessary under poor light conditions.
Foliage: Alternate, horizontal and in normal abundance.
*Leaf size.*—Medium. About 4 to 6 inches long and about $2\frac{1}{4}$ to $4\frac{1}{2}$ inches wide.
*Leaf shape.*—Substantially ovate, some with acuminate tip, and most leaves having one or two serrations on each side of the petiole.
*Aspect.*—Upper side — dull with vein indented. Under side — dull with ordinary veining.
*Color.*—Upper side — between 137A and 147A. Under side — near 137C.
*Retention.*—The foliage persists well when the plant is kept at low room temperatures, i.e., below 20° C., and with good light intensity.
Bracts: Generally about 15 to 20 in number, in overlapping arrangement with a tight center providing a full effect.
*Size.*—Varies, up to 7 inches long and 6 inches wide, some bracts being as wide as they are long.
*Shape.*—Ovate-acuminate with substantially entire margins but with some dentations. Small bracts are elliptical in shape.
*Petioles.*—Quite short, from $\frac{1}{4}$ inch to about 1 inch long.
*Ribs and veins.*—Veins are of a light creamy color and protrude from the under side of the bracts.
*Color.*—Bright Red, but somewhat lighter than Poinsettia V-14, with many small pink flecks and some pink streaks in the red of the bracts. Red: between 45C and 46C but slightly blued. The proper color is not shown in the R.H.S. Colour Chart. Pink: between RHS 47D and 51B but more greyed.
*Retention.*—The bracts have medium persistence.

This new plant has retained substantially all of the growth size and blooming characteristics of its parent, Poinsettia V-14, with the exception of foliage and bract coloration. The foliage of the new plant is somewhat darker in color than that of the parent and the red of the bracts is somewhat lighter than that of the parent. The new plant is particularly distinguished, however, by the very attractive pink flecks and streaks appearing on the background red of the bracts, thus providing a very unusual and attractively variegated, generally red poinsettia plant.

I claim:

1. A new and distinctive variegated red and pink poinsettia plant, substantially as herein shown and described, distinguished by the pink flecks and streaks appearing in the overall red background of the bracts, and by the retention of substantially all of the physical and growth characteristics, except foliage and bract coloration, of its parent, Poinsettia V-14.

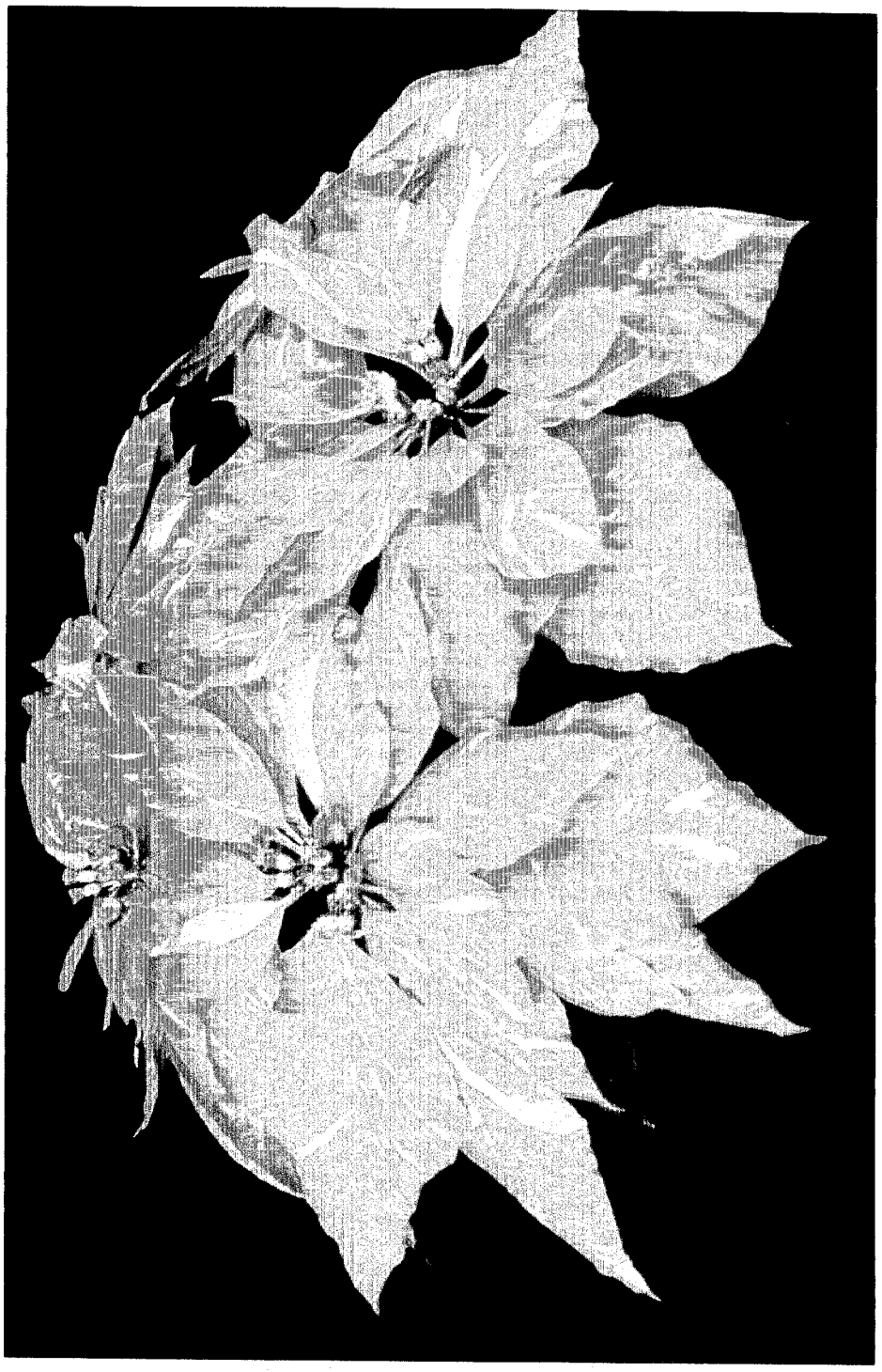

* * * * *